United States Patent [19]

Lesh et al.

[11] Patent Number: 5,385,148

[45] Date of Patent: Jan. 31, 1995

[54] CARDIAC IMAGING AND ABLATION CATHETER

[75] Inventors: Michael D. Lesh, Mill Valley; Patrick M. Owens, Cupertino; Jerome Jackson, Sunnyvale, all of Calif.

[73] Assignee: The Regents of the University of California, Oakland, Calif.

[21] Appl. No.: 99,995

[22] Filed: Jul. 30, 1993

[51] Int. Cl.$^6$ .............................................. A61B 8/00
[52] U.S. Cl. ........................... 128/662.06; 128/660.03
[58] Field of Search .................. 128/660.03, 662.03, 128/662.04, 662.05, 662.06, 898; 606/28

[56] References Cited

U.S. PATENT DOCUMENTS

| | | | |
|---|---|---|---|
| 3,938,502 | 2/1976 | Bom | 128/2 V |
| 4,327,738 | 5/1982 | Green et al. | 128/662.06 |
| 4,576,177 | 3/1986 | Webster, Jr. | 128/660 |
| 4,587,972 | 5/1986 | Morantte, Jr. | 128/660 |
| 4,641,649 | 2/1987 | Walinsky et al. | 128/303.1 |
| 4,747,405 | 5/1988 | Leckrone | 128/303.1 |
| 4,760,845 | 8/1988 | Kovalcheck | 128/303.1 |
| 4,790,311 | 12/1988 | Ruiz | 128/303.1 |
| 4,796,622 | 1/1989 | Lu et al. | 606/28 |
| 4,807,620 | 2/1989 | Strul et al. | 128/303.1 |
| 4,832,048 | 5/1989 | Cohen | 128/786 |
| 4,887,605 | 12/1989 | Angelsen et al. | 128/660.03 |
| 4,924,863 | 5/1990 | Sterzer | 606/27 |
| 4,936,281 | 6/1990 | Stasz | 128/660.03 |
| 4,940,064 | 7/1990 | Desai | 128/784 |
| 4,945,912 | 8/1990 | Langberg | 128/642 |
| 4,955,377 | 9/1990 | Lennox et al. | 128/401 |
| 4,960,134 | 10/1990 | Webster, Jr. | 128/786 |
| 4,998,933 | 3/1991 | Eggers et al. | 606/41 |
| 5,029,588 | 7/1991 | Yock et al. | 28/662.06 |
| 5,047,025 | 9/1991 | Taylor et al. | 606/31 |
| 5,056,517 | 10/1991 | Fenici | 128/419 P |
| 5,057,105 | 10/1991 | Malone et al. | 606/28 |
| 5,156,613 | 10/1992 | Sawyer | 128/898 |
| 5,158,087 | 10/1992 | Gatzke | 128/662.03 |
| 5,259,385 | 11/1993 | Miller et al. | 128/662.04 |

OTHER PUBLICATIONS

Kuck, K. H., et al., "Radiofrequency Current Catheter Ablation of Accessory Atrioventricular Pathways," Lancet, 337: 1557-61 (1991).

Bom, N., et al., "Early and Recent Intraluminal Ultrasound Devices," Inter. J. of Cardiac Imaging, 4: 79-88 (1989).

Breyer, B., et al., "Possibilities of Ultrasound Catheters," Inter. J. of Cardiac Imaging, 6: 277-284 (1991).

Breyer, B., et al., "Properties of Ultrasonically Marked Leads," PACE, vol. 12: 1369-1380 (Aug. 1969).

Ayisi, K., et al., "Alcohol-Induced Coagulation Necrosis in Cardiac Tissue: A New Concept in the Surgical Management of Recurrent Ventricular Arrhythmias," Thoracic Cardiovas. Surgeon, 37: 76-79 (1989).

Landzberg, J. S., et al., "The Transponder System: A New Method of Precise Catheter Placement in the Right Atrium Under Echocardiographic Guidance," JACC, vol. 12, No. 3: 753-756 (1988).

Langberg, J. J., et al., "The Echo-Transponder Electrode Catheter: A New Method for Mapping the Left Ventricle," JACC, vol. 12, No. 1: 218-223 (Jul. 1988).

Primary Examiner—George Manuel
Attorney, Agent, or Firm—Townsend and Townsend Khourie and Crew

[57] ABSTRACT

Method and apparatus for ablation of cardiac tissue includes a catheter (2, 60) having an elongated flexible body (6, 64), a tissue characterization assembly including a transducer (34) at the distal end (16) of the body and a tissue ablation assembly having a tissue ablation tip (32) at the distal end of the body. The tissue ablation tip is positioned adjacent the tissue to be ablated using the visualization assembly and then activated.

4 Claims, 3 Drawing Sheets

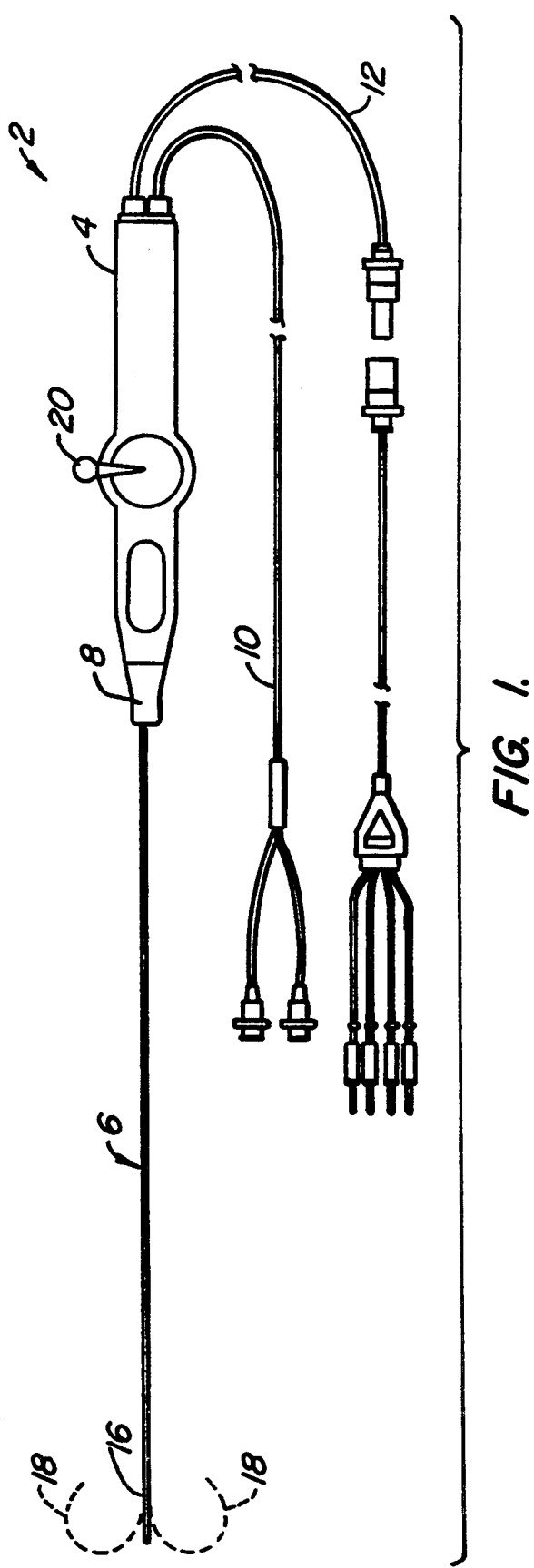
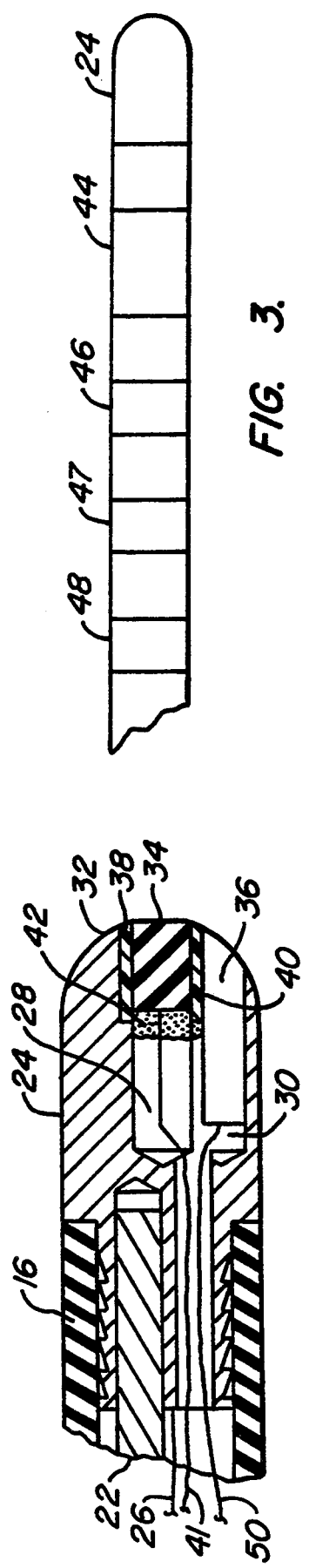
FIG. 1.
FIG. 2.
FIG. 3.

CARDIAC IMAGING AND ABLATION CATHETER

BACKGROUND OF THE INVENTION

Abnormal heart beats or cardiac arrhythmias can cause significant morbidity and mortality. These arrhythmias arise from a variety of causes, including atherosclerotic heart disease, ischemic heart disease, metabolic or hemodynamic derangements, rheumatic heart disease, cardiac valve disease, certain pulmonary disorders and congenital etiologies. The normal heart rate is about 60 to 100 beats per minute. Arrhythmias refer to tachycardias at rates exceeding 100 beats per minute for a duration of at least 3 beats. Sometimes no treatment is required, such as in the tachycardia following a physiologic response to stress or exercise. However, in some cases, treatment is required to alleviate symptoms or to prolong the patient's life expectancy.

A variety of treatment modalities exist, including electric direct current cardioversion, pharmacologic therapy with drugs such as quinidine, digitalis, and lidocaine, treatment of an underlying disorder such as a metabolic derangement, and ablation by either percutaneous (closed chest) or surgical (open chest) procedures. Treatment by ablation involves destruction of a portion of cardiac tissue which is functioning abnormally electrically.

Normally the heart possesses an intrinsic pacemaker function in the sinoatrial (SA) node which is in the right atrium, adjacent to the entrance of the superior vena cava. The right atrium is one of four anatomic chambers of the heart. The other chambers are the right ventricle, the left atrium, and the left ventricle. The superior vena cava is a major source of venous return to the heart. The SA node is an area of specialized cardiac tissue called Purkinje cells and which usually measures roughly 1½ centimeters by about 2½ millimeters. An electrical impulse normally exits from the SA node and travels across the atrium until it reaches the atrioventricular (AV) node. The AV node is located in the right atrium near the ventricle.

Emerging from the AV node is a specialized bundle of cardiac muscle cells which originate at the AV node in the interatrial septum. This "bundle of His" passes through the atrioventricular junction and later divides into left and right branches which supply the left and right ventricles. The left and right bundles further give rise to branches which become the so-called distal His-Purkinje system, which extends throughout both ventricles.

Thus in a normal situation an impulse originates intrinsically at the SA node, transmits through the atrium and is modified by the AV node. The AV node passes the modified impulse throughout the left and right ventricles via the His-Purkinje system to result in a coordinated heartbeat at a normal rate.

Many factors affect the heart rate in addition to the intrinsic conduction system. For example, normally the heart rate will respond to physiologic parameters such as stress, exercise, oxygen tension and vagal influences. Additionally, there are multiple causes for an abnormal heartbeat such as an abnormal tachycardia. One group of such causes relates to abnormalities in the heart's conduction system. For example, ectopic or abnormally positioned nodes may take over the normal function of a node such as the SA or AV node. Additionally, one of the normal nodes may be diseased such as from ischemic heart disease, coronary artery disease or congenital reasons. Similarly, a defect can exist in an important part of the conduction system such as the bundle of His or one of the bundle branches supplying the ventricles.

Treatment of abnormal tachycardias arising from ectopic foci or so-called ectopic pacemakers can include pharmacologic therapy or ablative therapy. The ablative therapy may be accomplished by percutaneous insertion of a catheter or by an open surgical cardiac procedure.

Cardiac arrhythmias may be abolished by ablating the tissue responsible for the genesis and perpetuation of the arrhythmias. Ablation catheters using radio frequency (RF) energy are known. Additionally ethanol has been infused into coronary arteries to ablate a focus such as a ventricular arrhythmia focus or the AV node. Unfortunately this tends to result in a fairly large region of cardiac tissue death or myocardial infarction. With transarterial infusion there is difficulty in precisely controlling the location and extent of the ablation.

During conventional ablation of cardiac tissue in attempts to ablate arythmogenic foci, such as the AV node, AV node reentry, Wolff-Parkinson-White, and ventricular tachycardia foci, it is difficult to know the size and extent of the lesion being created. With RF energy, electrode tip temperature serves as a rough guide that a lesion is being created and as to the size or volume of the lesion. However, variation in the angle of the tip with respect to the tissue and the rapidity of blood movement among other factors makes this a very rough, indirect guide at best.

Normally when performing a percutaneous or closed chest cardiac ablation procedure, fluoroscopy is used to visualize the chambers of the heart. Fluoroscopy uses roentgen rays (X-rays) and includes use of a specialized screen which projects the shadows of the X-rays passing through the heart. Injectable contrast agents to enhance the fluoroscopic picture are known.

Some of the problems with conventional fluoroscopic positioning of catheters include prolonged radiation exposure, sometimes as long as 2 hours. Additionally, the clinician may be unable to determine precisely where the catheter is in terms of the endocardium and cardiac structures, such as valves. Additionally, the tissue is not characterized before or after ablation except in electrical terms. The thickness or volume of the tissue is not assessed.

Thus, the prior art lacks methods and devices useful for precisely ablating cardiac tissue and accurately determining the extent of the lesion being created. The present invention addresses these and other needs.

SUMMARY OF THE INVENTION

The present invention is directed to a method and apparatus for ablation of cardiac, and other, tissue which combines the use of both a tissue characterization assembly with a tissue ablation assembly into one catheter. This permits the user to characterize the area being ablated to provide almost instantaneous feedback on the amount of tissue being ablated, and the location of that tissue, to help prevent the destruction of too much or too little tissue. This can be carried out using generally conventional tissue characterization and ablation devices; the invention can also use a novel hollow injecting needle, which can be imbedded in and become secured to the tissue to be ablated, using fluid ablation techniques.

The method for ablation of tissue includes selecting a catheter having: an elongated flexible body, a tissue characterization assembly including a transducer at the distal end of the body, and a tissue ablation assembly having a tissue ablation tip at the distal end of the body. The distal end of the catheter is introduced into a cardiac chamber (or other body region) including the tissue to be ablated. The tissue characterization assembly is used to position the tip of the tissue ablation assembly adjacent the tissue to be ablated. Once in position, the ablation assembly is activated to ablate the tissue in question. The ablation assembly may comprise any of a number of standard ablation means such as radio frequency (RF) energy, microwave energy, laser, DC, cryoablation and the like. In a preferred embodiment described below, RF is used.

Alternatively, two catheters may be used in the method. In this embodiment, each function, tissue characterization and ablation, are provided by a separate catheter. Both catheters are introduced into the same or different chamber and monitoring of ablation is carried out as described above.

The invention can be used with the hollow injecting needle having a securing element configured to engage tissue when the needle is at least partially inserted into the tissue to help prevent inadvertent removal of the needle from the tissue. The securing element can be configured into the form of a corkscrew-shaped needle. Other structures, such as barbs, could also be used as the securing element. This permits the ablation liquid to be directed at a specific site impaled by the needle to help prevent the undesired destruction of surrounding tissue. The invention can be used with conventional ablation compounds such as alcohol (e.g., ethanol), collagen, phenol, carbon dioxide and the like. Endocardial infusion needles suitable for use in the present invention are disclosed in copending application, U.S. Ser. No. 08/100,086, which is incorporated herein by reference.

Another feature of the invention is the use of a thermal insulating layer surrounding at least part of the ultrasound transducer. This is important when the ultrasound transducer is surrounded by an ablation tip which heats up during use, such as occurs with a radio frequency transmitting ablation tip.

The present invention provides the novel combination of tissue ablation and tissue characterization in a single catheter to permit ablation of tissue to be properly accomplished by the correct selection of the ablation site and monitoring and controlling the ablation of the tissue being destroyed. The invention is preferably used with ultrasonic transceivers in an ablation catheter to provide real time assessment of lesion volume and to monitor the tissue being ablated. This results in the ability to closely control, to a much greater degree than presently possible, the ablation of tissue so that only that tissue desired to be ablated is destroyed.

In practice, a catheter of the invention is placed in an artery or a vein of the patient depending on whether the left (ventricle and/or atrium) or right (ventricle and/or atrium) side of the heart is to be explored and portions thereof ablated. Frequently an artery or vein in the groin such as one of the femoral vessels is selected for catheterization. The catheter is passed via the blood vessel to the vena cava or aorta, also depending on whether the right or left side of the heart is to be catheterized, and from there into the appropriate atrium and/or ventricle.

The catheter is generally steerable and it is positioned against an endocardial region of interest. In addition to an ultrasound transducer, the catheter typically includes a means for sensing the electrical impulses originating in the heart. Thus, the electrode catheter can provide a number of readings from different areas of the internal aspects of the heart chambers. These various readings are correlated to provide an electrophysiologic map of the heart including notation of normal or abnormal features of the heart's conduction system. Once the electrophysiologic map is produced, an area may be selected for ablation.

Before final ablation, the suspect area can be temporarily suppressed or deadened with a substance such as lidocaine or iced saline solution. Subsequently the area is remapped and the heart reevaluated to determine if the temporary measure has provided some electrophysiologic improvement. If improvement has occurred, then the clinician may proceed with permanent ablation typically using RF radiation.

Other features and advantages of the invention will appear from the following description in which the preferred embodiments have been set forth in detail in conjunction with the accompanying drawings.

BRIEF DESCRIPTION OF THE DRAWINGS

FIG. 1 is an overall view of a catheter made according to the invention;

FIG. 2 is an enlarged, simplified cross-sectional view of the distal end of the flexible body of FIG. 1;

FIG. 3 is an enlarged, schematic view of the distal end of the flexible body of FIG. 1 illustrating the general locations of the tip electrode, ultrasonic transducer, and ring electrodes.

DESCRIPTION OF THE PREFERRED EMBODIMENT

Figure 4:
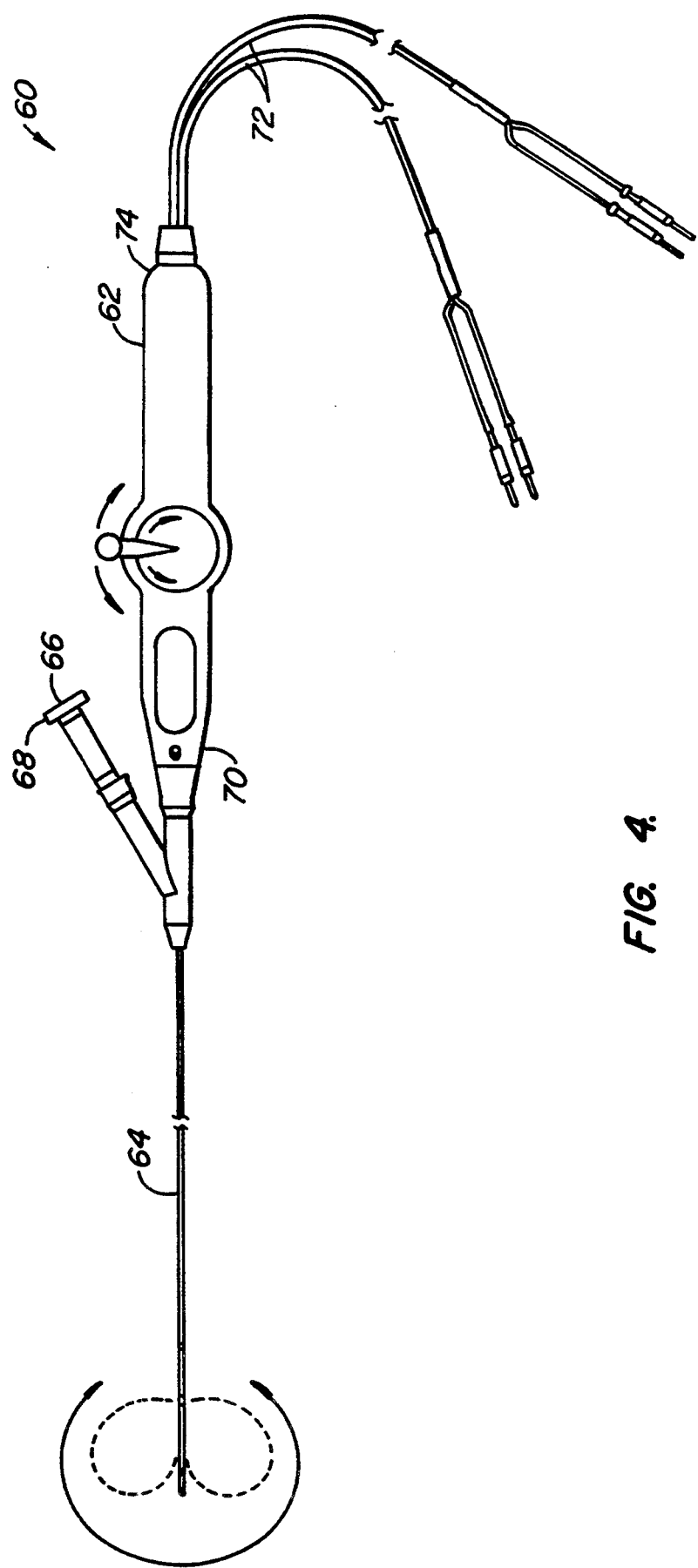
FIG. 4 is an overall view of an alternative catheter made according to the invention.

FIG. 1 illustrates a catheter 2 having a handle 4 from which a flexible body 6 extends. Flexible body 6 extends from one end 8 of handle 4 while ultrasonic cable 10 and a combination electrode/thermistor cable 12 extend from the other end 14 of handle 4. Distal end 16 of flexible body 6 is steerable, as suggested by the dashed lines 18 in FIG. 1, in a conventional manner using a steering lever 20 mounted to handle 4. Lever 20 which controls one or more steering cables 22, see FIG. 2, as is conventional. Distal end 16 has an RF transmitting tip 24 secured thereto. Transmitting tip 24 is connected to an appropriate RF energy source, not shown, through lead 26 which extends along flexible body 6, through handle 4 and through combined cable 12.

Tip 24 has a pair of axially extending bores 28, 30 formed from its distal end 32. Bore 28 is used to house an ultrasonic transducer 34 while bore 30 is used to house a thermistor 36. Transducer 34 is surrounded by a thermal insulating sleeve 38, typically made of insulating material such as polyimide. The base 40 of transducer 34 has a lead 41 extending from transducer 34, along flexible body 6, through handle 4 and through ultrasonic cable 10. The ultrasonic transducer 34 comprises a piezoelectric crystal capable of operating at a standard frequency, typically from about 5 to about 50 MHz. The crystal is formed from standard materials such as barium titanate, cinnabar, or zirconate-titanate. The transducer 34 generates an ultrasonic pulse in response to electrical impulses delivered through lead 41. Ultrasonic echoes are then received by the ultrasonic transducer 34 which generates electrical signals which are delivered to the receiving unit (not shown). The transducer 34 is connected to conventional transmitting and receiving units which include the circuitry necessary for interpreting the ultrasonic information and displaying the information on a visual display. Signal processing may take advantage of change in tissue density or texture as correlated with lesion depth. The ultrasonic signal can be visualized on a two dimensional echocardiograph or using non-imaging A-mode display.

Base 40 of transducer 34 is sealed with a UV potting adhesive 42, such as Tough Medical Bonder made by Loctite, to provide both thermal and electrical insulation. The catheter also comprises an ultrasonic transponder 44, shown schematically in FIG. 3, spaced about 2.5 mm from RF transmitting tip 24 at the distal end 16 of body 6. Transponder 44 is used to help in localization of the catheter tip as is known in the art and described by Langberg et al., *JACC* 12:218-223 (1988). In alternate embodiments, multiple transponders can be used to help with assessing catheter tip orientation as well.

In the embodiment of FIGS. 1–3, the ablation apparatus exemplified by the use of RF transmitting tip 24. In addition to tip electrode 24, catheter 2 also includes three ring electrodes 46, 47, 48 positioned in a proximal direction, that is towards handle 4 relative to tip electrode 24 and transducer 44. Electrodes 46–48 (spaced 2.5 mm apart) are used to record electrical signals produced by the heart (electrocardiograms) for endocardial mapping using a multichannel EKG machine as is known in the art. Temperature monitoring means such as a thermistor 36 is coupled to combination cable 12 through a lead 50 extending from thermistor 36, to flexible body 6, through handle 4 and into combination cable 12. The thermistor 36 is used to provide information about the temperature of the tissue at the distal end 32 of tip 24. The temperature monitoring means can alternatively be a thermocouple, a fiber optic temperature monitor, and the like.

Separately, the above-discussed apparatus used to create ultrasonic characterization of the tissue to be ablated is generally conventional. As discussed above, the ultrasonic characterization means may be used for either imaging or A-mode. One such ultrasonic imaging system is sold by Cardiovascular Imaging systems of Sunnyvale, Calif. Similarly, the RF ablation system, used to ablate the tissue, is also generally conventional, such as is sold, for example, by EP Technologies of Sunnyvale, Calif. What is novel is incorporating both the tissue characterization and ablation structure into a single catheter which permits real time characterization and accurate positioning of the RF transmitter tip 24 with the precise location to be ablated. The amount or volume of tissue ablated can thus be constantly monitored during the procedure so that neither too little nor too much tissue is ablated for maximum control and effectiveness. The use of temperature monitoring using thermistor 36 is also generally conventional as well, but not in conjunction with an ultrasonic assembly. Instead of using RF energy to ablate the tissue, microwave radiation, laser energy, cryoablation or endocardial injection/infusion, for example, can be used in conjunction with ultrasonic transducer 34.

Figure 5:
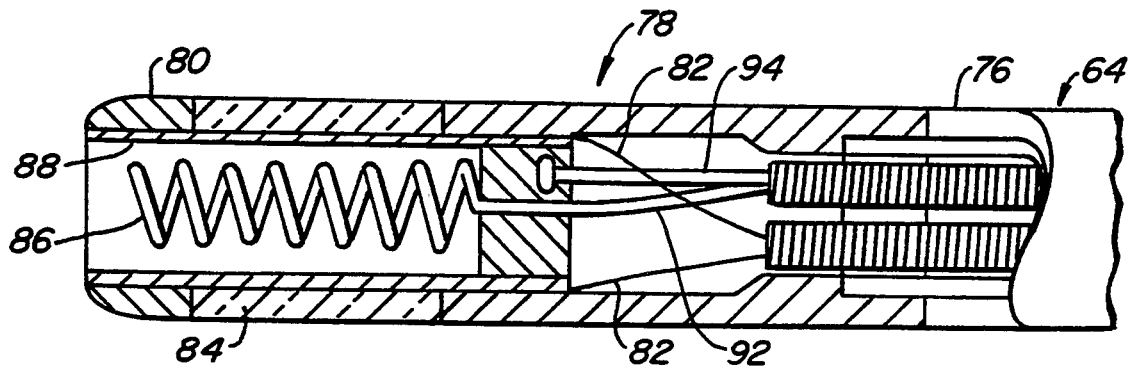
FIG. 5 is an enlarged, simplified cross-sectional view of the tip and the catheter of FIG. 4, shown with a hollow needle retracted.
Figure 6:
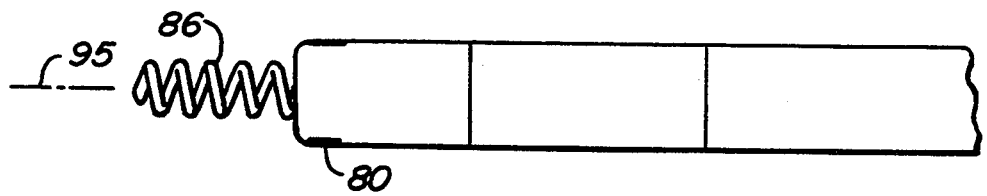
FIG. 6 is an external view of the tip of FIG. 5 with the hollow needle extended.
Figure 7:
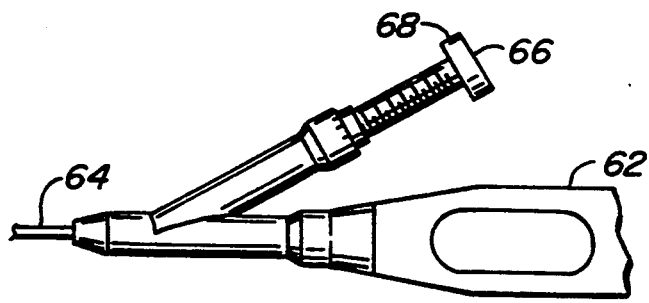
FIG. 7 is an enlarged view of the needle driver and infusion port mounted to the handle of FIG. 4.

Referring the reader now to FIGS. 4–7, a catheter 60 is shown. Catheter 60 includes a handle 62 from which a flexible body 64 extends. Handle 62 includes a steering lever 65 and combination infusion port 66 and needle driver 68 at the distal end 70 of handle 62. A pair of cables 72 extend from the proximal end 74 of handle 62. The distal end 76 of flexible body 64 has a tip assembly 78 mounted thereto. Tip assembly 78 includes mapping electrodes 80 connected to wires 82 which extend down flexible body 64, through handle 62 and to cables 72. Mapping electrodes 80 provide the user with a nonvisual indication of where tip assembly is by monitoring the electro-activity of the heart muscle, as is conventional. Electrodes 80 are electrically isolated from the remainder of tip assembly 78 by an insulating sleeve 84.

A hollow needle 86 is slidably mounted within a second insulating sleeve 88 housed within insulating sleeve 84. The needle may be formed from standard metal alloys such as titanium alloy, stainless steel, and cobalt steel. The needle 86 is a corkscrew-shaped needle used to inject ablating liquid into tissue and secure the needle to the tissue. Other designs of hollow needles, including the use of barbs on a straight or curved needle, can be used as well. While hollow needle 86 is shown used with a generally conventional mapping electrode type of catheter, it could be used with an ultrasonic assembly as shown in FIGS. 1–3, as well as other types of tissue characterization assemblies.

A central bore 90 of hollow needle 86 is coupled to infusion port 66 by an injection fluid tube 92 which extends along flexible body 64, through needle driver 68 and to infusion port 66. Threaded needle driver 68 is connected to a tip extension 94 so that rotating needle driver 68 causes tip extension 94 to rotate about the axis 95 of needle 86 and to move axially within flexible body 64. This causes hollow needle 86 to rotate about axis 95 and to move axially within sleeve 88 from the retracted position of FIG. 5 to the extended position of FIG. 6.

Rotating needle driver 68 also rotates hollow needle 86 so that it bores into the tissue to be ablated. When properly in position, an appropriate liquid, such as ethanol, can be infused into the tissue to be ablated through infusion port 66, injection fluid tube 92, hollow needle 86, and into the tissue. Since the tip 100 of hollow needle 86 is buried within the tissue to be ablated, the operator is assured that the ablation liquid is delivered to the proper place while minimizing ablation of surrounding tissue.

The use of catheter 2 proceeds generally as follows. Distal end 16 of body 6 is directed to the appropriate site using conventional techniques and steering lever 20. Characterization of the tissue to be ablated and localization of the tip 24 are provided by ultrasonic transducer 34, ultrasonic transponder 44, and associated leads and cables coupled to a conventional ultrasonic console, not shown. When tip 24 is at the site of the tissue to be ablated, RF generator, not shown, coupled to combination cable 12, is activated to produce RF radiation at tip 24 to ablate the tissue. The ablation is monitored by ultrasonic transducer 34 as well as thermistor 36 to help ensure that the proper volume of tissue is ablated. When the proper volume of tissue is ablated, body 6 is removed from the patient. Instead of the use of catheter 2 including an RF transmitter tip 24, the catheter could use an ablation fluid injecting tip similar to that shown in FIGS. 4–7. Also, preparatory to the ablation sequence, the suspect area can be temporarily suppressed or deadened using catheter 60 using lidocaine or iced saline solution, as discussed in the Background section above.

Modification and variation can be made to the disclosed embodiments without departing from the subject of the invention as defined in the following claims.

What is claimed is:

1. A method for ablation of arrythmogenic cardiac tissue comprising:
   selecting a catheter comprising:
      an elongated flexible body having a proximal end and a distal end,
      an ultrasound assembly having a transducer located at the distal end of the body, and
      a tissue ablation means;
   introducing the distal end of the catheter into a cardiac chamber comprising the arrythmogenic cardiac tissue to be ablated;
   using the ultrasound assembly to position the tissue ablation means within an effective range of the arrythmogenic cardiac tissue to be ablated; and
   activating the tissue ablation means.

2. The method of claim 1, wherein the step of selecting the catheter further includes selecting a catheter having tissue ablation means including means for delivering electromagnetic radiation.

3. The method of claim 1, further comprising the step of monitoring the ablation of the tissue using the ultrasound assembly, so that only desired tissue is ablated.

4. The method of claim 1, wherein the step of activating the ablation means includes delivering electromagnetic radiation selected from the group consisting of radio frequency, laser, and microwave radiation.

* * * * *